United States Patent [19]
Labarthe

[11] Patent Number: 5,348,885
[45] Date of Patent: Sep. 20, 1994

[54] CULTURE DISH

[76] Inventor: Jean-Christophe Labarthe, 1, rue Godard, 72000 Le Mans, France

[21] Appl. No.: 6,031

[22] Filed: Jan. 19, 1993

[30] Foreign Application Priority Data

Jan. 30, 1992 [FR] France .................. 92 01013

[51] Int. Cl.[5] .............. C12M 1/28; C12M 1/22; C12M 1/16
[52] U.S. Cl. ................... 435/294; 435/298; 435/299; 435/30; 220/290; 220/293
[58] Field of Search ............ 220/290, 293-302; 435/30, 292, 294, 293, 297, 298, 299-301; 422/102

[56] References Cited

U.S. PATENT DOCUMENTS

| | | | |
|---|---|---|---|
| 2,257,715 | 9/1941 | Hopkins | 220/293 |
| 3,474,004 | 10/1969 | Fink | 435/298 |
| 3,907,647 | 9/1975 | Sanderson | 435/294 |
| 4,072,577 | 2/1978 | Hirshaut . | |
| 4,461,836 | 7/1984 | Von Froreich | 435/294 |
| 4,675,298 | 6/1987 | Brusewitz | 435/298 |

FOREIGN PATENT DOCUMENTS

| | | |
|---|---|---|
| 0066199 | 8/1982 | European Pat. Off. . |
| 0171174 | 2/1986 | European Pat. Off. . |
| 1572527 | 6/1969 | France . |
| 2639957 | 12/1988 | France . |

*Primary Examiner*—William H. Beisner
*Attorney, Agent, or Firm*—Pearne, Gordon, McCoy & Granger

[57] ABSTRACT

This culture dish comprises an axisymmetric receptacle (1) having a bottom on which is disposed a layer (2) of a culture medium and a movable lid (5), covering the receptacle (1) and having an internal face from which emerges a spreader (9), and structures associated with the receptacle and lid making it possible to transfer the lid (5) from a depositing position in which the spreader (9) is distant from the layer (2) to a spreading position in which it touches the layer (2), and which the structures are arranged such that the transfer requires two movements, in different directions, with respect to the receptacle (1), to be imparted to the lid (5).

7 Claims, 2 Drawing Sheets

CULTURE DISH

BACKGROUND OF THE INVENTION

French Patent No. 88 16 053 describes a culture dish intended for culturing microorganisms, comprising a receptacle which is covered by a lid and on the bottom of which there is disposed a layer of a culture medium and a spreader emerging from an internal face of the lid and intended to spread an inoculum over the layer. The lid is mounted movably on the receptacle so as to be able to transfer from a depositing position, in which the spreader is distant from the layer, to a spreading position in which it touches the layer.

After having performed the spreading and having returned to the depositing position, it is possible to pass involuntarily from the depositing position to the spreading position. The raised parts of colonies which are formed are thus scraped, which vitiates the subsequent evaluation.

SUMMARY OF THE INVENTION

The invention overcomes this drawback by using a culture dish, comprising an axisymmetric receptacle on the bottom of which is disposed a layer of a culture medium and which is covered by a movable lid, from one of the internal faces of which emerges a spreader, and means making it possible to transfer the lid from a depositing position in which the spreader is distant from the layer to a spreading position in which it touches the layer, characterised in that the means for transferring the lid from the depositing position to the spreading position are arranged such that the transfer requires two movements, in different directions, with respect to the receptacle, to be imparted to the lid.

It is possible to transfer from the depositing position to the spreading position only by deliberate actions, which prevents accidental or inadvertent return to the spreading position from the depositing position.

In order to facilitate handling, provision is made for the first movement to be a rotational movement with respect to the axis of the receptacle, since the user has a natural tendency, when starting a manoeuvre, to perform a rotational movement of this kind.

Safety is even greater if the means for transfer of the lid from the depositing position to the spreading position are arranged such that the transfer requires three movements, two successive movements being, whatever the movements in question, in different directions. One of the movements may be a rotation around the axis of the receptacle and the other movement a translation parallel to the axis of the receptacle.

According to an embodiment which is particularly easy to produce and to use, the means for transfer into the spreading position comprise a peripheral rib made on the external lateral face of the receptacle and interrupted by at least two notches angularly distributed in a regular manner and, associated respectively with each notch, a lowering stud emerging from the internal lateral face of the lid, at a distance from the upper part of the lid which is greater than the distance between the upper rim of the receptacle and the rib.

In order to prevent any untimely lowering when the lid has been turned, and is situated opposite the notch through which it may go into the spreading position, lowering stops are provided which emerge from the lateral face of the receptacle and are associated respectively with each notch, each lowering stop being disposed beneath the notch at a distance greater than the dimension, along the axis of the receptacle, of the lowering stud and extending along the periphery over an arc extending on either side beyond the notch. In order to make the lowering of the lid more gradual and to make the bringing of the spreader into contact with the culture layer less abrupt, each lowering stop comprises an end slope inclined downwards.

In order also to prevent inadvertent transfer from the depositing position to an opening position, and therefore untimely opening of the dish, there are provided means for transfer of the lid from the depositing position to the opening position, these means being arranged such that this transfer requires two relative movements in different directions, with respect to the receptacle, to be imparted to the lid. These means for transfer into the opening position may comprise the peripheral rib made on the external lateral face of the receptacle and interrupted by at least two notches angularly distributed in a regular manner and, associated with each notch a raising head emerging from the internal lateral face of the lid. For greater safety, raising stops are provided emerging from the lateral face of the receptacle and respectively associated with each notch, each raising stop being disposed above the notch at a distance greater than the dimension, along the axis of the receptacle, of the raising stud and extending along the periphery of an arc extending on either side beyond the notch. The raising stud is further away than the lowering stud associated with the same notch from the upper part of the lid by a distance at least equal to the dimension, along the axis of the receptacle, of the rib and the two studs are offset with respect to each other by an angular distance corresponding to a peripheral distance greater than the peripheral length of the notch and less than 360°/n, n being the number of notches.

BRIEF DESCRIPTION OF THE DRAWINGS

In the attached drawing, which is given solely by way of example.

DESCRIPTION OF THE PREFERRED EMBODIMENTS

Figure 1:
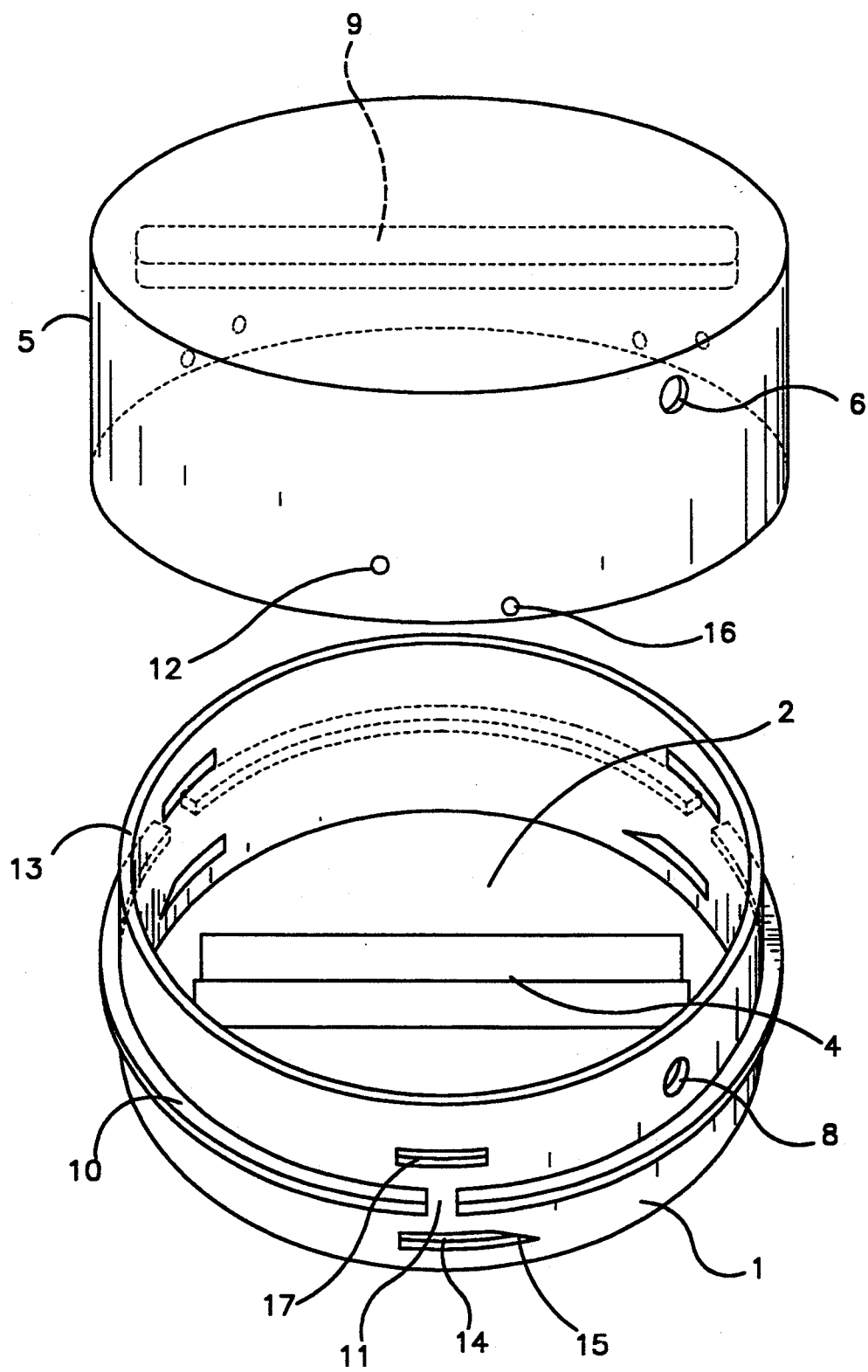
FIG. 1 is an exploded perspective view of a dish according to the invention.

The culture dish according to the invention comprises an axisymmetric receptacle 1. On the upper face of the bottom of the receptacle is disposed a layer 2 of agar. A gripping means 4 is provided on the lower face of the bottom.

The receptacle 1 is covered by a lid 5 comprising an opening 6 which can be made to coincide with an opening 8 of the receptacle 1, by rotating the lid 5 on the receptacle 1. A spreader 9 projects from the internal face of the upper part of the lid 1.

A peripheral rib 10 interrupted by three notches 11 at 120° to each other runs over the external lateral face of the receptacle 1. Three lowering studs 12, respectively associated with each notch 11 emerge from the internal lateral face of the lid 5, which studs are situated at a distance from the upper part of the lid carrying the spreader 9 which is greater than the distance between the upper rim 13 of the receptacle and the rib 10.

A lowering stop 14 is provided beneath each notch 11. Each stop 14 is at a distance from the notch 11 corresponding to it which is greater than the dimension along the axis of the receptacle of the lowering stud 12 and it extends along the periphery over an arc extending beyond the notch 11 on either side. Each stop comprises an end slope 15 inclined downwards.

A raising stud 16 offset by 20° with respect to the corresponding stud 12 emerges from the internal lateral face of the lid, in the same way for each notch 11. A raising stop 17 emerging from the lateral face of the receptacle 1 is associated with each notch 11. Each raising stop 17 is disposed above the corresponding notch 11, at a distance greater than the dimension, along the axis of the receptacle, of the raising stud 16 and extends, along the periphery, over an arc extending beyond the notch 11 on either side. The raising stud 16 is further away than the lowering stud 12 from the upper part of the lid 5 by a distance at least equal to the dimension, along the axis of the receptacle, of the rib 10.

Figure 2:
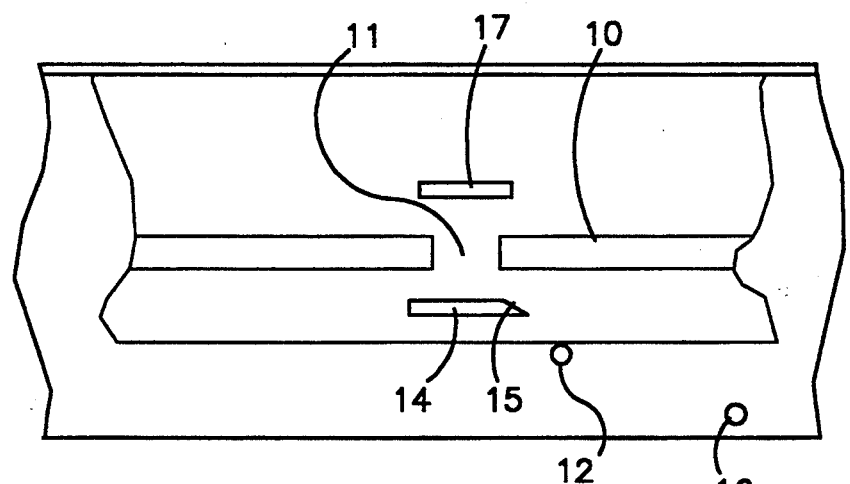
FIGS. 2 to 4 are partial plan views illustrating the operation of the dish.
Figure 3:
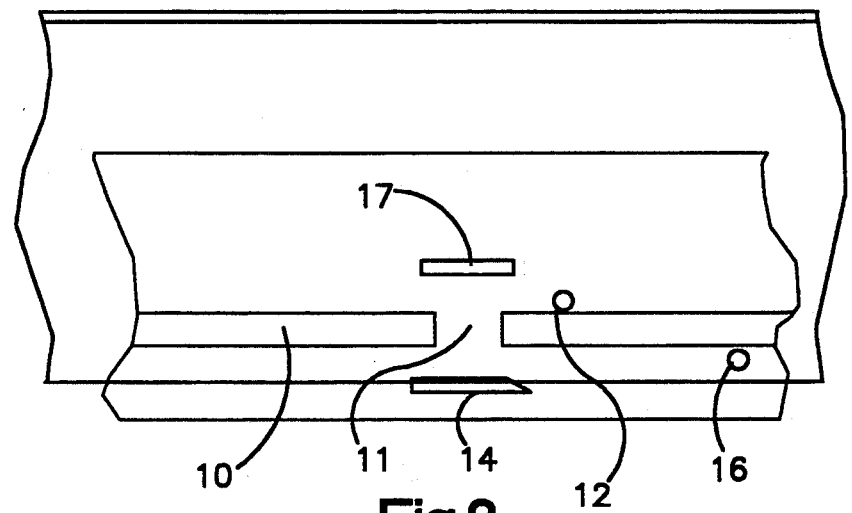
Figure 4:
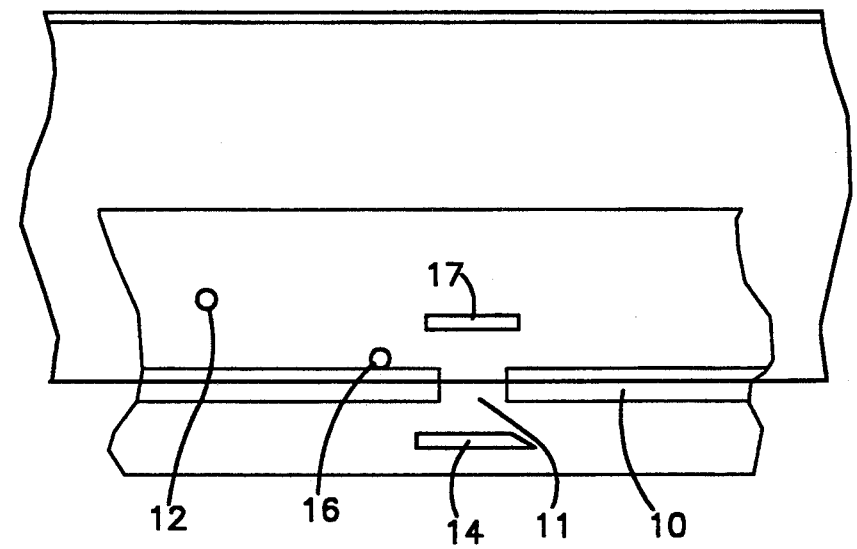

Transfer from the depositing position illustrated in FIG. 3 to the spreading position illustrated in FIG. 2, takes place by turning the lid 5 until the lowering stud 12 is opposite the notch 11 and, by passing through the latter, is placed beneath the rib 10. After this translational movement of the lid, a rotational movement is performed during which the stud 12 slides over the stop 14 and the slope 15, so that the spreader 9 comes into contact with the agar-covered layer.

Once the spreading has been performed, the lid is returned to the depositing position illustrated in FIG. 3 by movements which are the reverse of those which made it possible to transfer from the depositing position to the spreading position.

In order to open the dish, starting from the depositing position, the lid is turned so as to bring the raising stud 16 opposite the notch 11. The lid is lifted. The raising stud 16 passes into the notch and comes above the rib 10, but beneath the raising stop 17. A new rotation is imparted to the lid in order to disengage the stud 16 from the stop 17. The lid can then be removed from the dish.

I claim:

1. A culture dish, comprising
an axisymmetric receptacle having an axis, an external lateral face, an upper rim and a bottom on which is disposed a layer of culture medium,
a movable lid covering the receptacle and having an upper part, an internal lateral face, and an internal face from which projects a spreader,
means to transfer the lid from a depositing position to a spreading position and to an opening position,
said means including a peripheral rib on the external lateral face of the receptacle and interrupted by at least two notches angularly distributed in a regular manner and, associated respectively with each notch, a lowering stud emerging from the internal lateral face of the lid, at a distance from the upper part of the lid which is greater than the distance between the upper rim of the receptacle and the rib, said rib, notches and lowering studs being arranged to transfer the lid from the depositing position in which the spreader is spaced from the layer to a spreading position in which the spreader touches the layer in a manner such that the transfer requires at least a first movement and a second movement, in different directions, with respect to the receptacle, to be imparted to the lid,
said means also including, associated respectively with each notch, a raising stud emerging from the internal lateral face of the lid, said raising stud being further away than the lowering stud associated with the same notch from the upper part of the lid by a distance at least equal to the dimension, along the axis of the receptacle, of the rib, said rib, notches and raising studs being arranged to transfer said lid from the depositing position to the opening position in which the lid can be removed in a manner such that the transfer requires at least a first movement and a second movement, in different directions, with respect to the receptacle, to be imparted to the lid.

2. The culture dish according to claim 1, in which the first movement to transfer the lid from the depositing position to the spreading position is a rotational movement with respect to the axis of the receptacle.

3. The culture dish according to claim 2, in which the transfer of the lid from the depositing position to the spreading position requires three movements to be successively imparted to the lid, any two successive movements of the three movements being in different directions.

4. The culture dish according to claim 3, in which one of the three movements is a rotational movement with respect to the axis of the receptacle and another of the three movements is a translation parallel to the axis of the receptacle.

5. The culture dish according to claim 1, wherein the external lateral face of the receptacle further includes a lowering stop disposed beneath each notch at a distance greater than the dimension, along the axis of the receptacle, of the lowering stud and raising stud associated with each notch and extending along the periphery of an arc extending on either side beyond the notch, said lowering stud and said raising stud associated with each notch being offset with respect to each other by an angular distance corresponding to a peripheral distance greater than the peripheral length of the notch and less than 360 degrees/n, n being the number of notches.

6. The culture dish according to claim 5, in which each lowering stop comprises an end slope inclined downwards.

7. The culture dish according to claim 1, wherein the external lateral face of the receptacle further includes a raising stop disposed above each notch at a distance greater than the dimension, along the axis of the receptacle, of the lowering stud and raising stud associated with each notch and extending along the periphery of an arc extending on either side beyond the notch, said lowering stud and said raising stud associated with each notch being offset with respect to each other by an angular distance corresponding to a peripheral distance greater than the peripheral length of the notch and less than 360 degrees/n, n being the number of notches.

* * * * *